(12) United States Patent
Ferrando et al.

(10) Patent No.: US 9,364,463 B2
(45) Date of Patent: Jun. 14, 2016

(54) USE OF AMINO ACID SUPPLEMENTATION FOR IMPROVED MUSCLE RECOVERY

(71) Applicant: The Board of Trustees of the University of Arkansas, Little Rock, AR (US)

(72) Inventors: Arny Ferrando, Little Rock, AR (US); Robert R. Wolfe, Little Rock, AR (US)

(73) Assignee: BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 74 days.

(21) Appl. No.: 14/359,213

(22) PCT Filed: Nov. 19, 2012

(86) PCT No.: PCT/US2012/065842
§ 371 (c)(1),
(2) Date: May 19, 2014

(87) PCT Pub. No.: WO2013/075095
PCT Pub. Date: May 23, 2013

(65) Prior Publication Data
US 2014/0343112 A1    Nov. 20, 2014

Related U.S. Application Data

(60) Provisional application No. 61/598,586, filed on Feb. 14, 2012, provisional application No. 61/561,524, filed on Nov. 18, 2011.

(51) Int. Cl.
*A61K 31/472* (2006.01)
*A61K 31/198* (2006.01)
*A61K 31/4172* (2006.01)
*A23L 1/305* (2006.01)
*A61K 31/405* (2006.01)

(52) U.S. Cl.
CPC ........... *A61K 31/4172* (2013.01); *A23L 1/3051* (2013.01); *A61K 31/198* (2013.01); *A61K 31/405* (2013.01); *A23V 2002/00* (2013.01)

(58) Field of Classification Search
CPC ................... A23V 2002/00; A23V 2200/316; A23V 2250/06; A23L 1/3051; A61K 31/198; A61K 31/405; A61K 31/4172
See application file for complete search history.

(56) References Cited

FOREIGN PATENT DOCUMENTS

WO    2013/075095 A1    5/2013

OTHER PUBLICATIONS

Ferrando et al., "EAA supplementation to increase nitrogen intake improves muscle function during bed rest in the elderly", Clinical Nutrition, 2010, pp. 18-23, vol. 29, No. 1.
Fiatarone et al., "Exercise training and nutritional supplementation for physical frailty in very elderly people", The New England Journal of Medicine, 1994, pp. 1769-1775, vol. 330, No. 25.
Gapeyeva et al., "Quadriceps femoris muscle voluntary isometric force production and relaxation characteristics before and 6 months after unilateral total knee arthroplasty in women", Knee Surg Sports Traumatol Arthrose, 2007, pp. 202-211, vol. 15, No. 2.

(Continued)

*Primary Examiner* — Savitha Rao
(74) *Attorney, Agent, or Firm* — Polsinelli PC (57) ABSTRACT

The present invention encompasses an amino acid composition for recovery of muscle strength and function.

18 Claims, 2 Drawing Sheets

(56) References Cited

OTHER PUBLICATIONS

International Search Report and Written Opinion from related International Application No. PCT/US2012/065842, dated Feb. 7, 2013; 11 pgs.

University of Arkansas for Medical Sciences, "Essential Amino Acid Supplementation for Recovery from Hip Surgery: Supporting clinical data", [online] Jul. 20, 2010 (retrieved Jan. 2, 2013]. Available on the internet: <URL: http://www.ibridgenetwork.org/uams/essential-amino-acid-supplementation-for-recovery-from-hip-su>.

Unver et al., "Ability to rise independently from a chair during 6-month follow-up after unilateral and bilateral total knee replacement", J. Rehabil. Med., 2005, pp. 385-387, vol. 37, No. 6.

USE OF AMINO ACID SUPPLEMENTATION FOR IMPROVED MUSCLE RECOVERY

INCORPORATION BY REFERENCE

This application claims priority to U.S. provisional applications 61/561,524, filed Nov. 18, 2011, and 61/598,586, filed Feb. 14, 2012, each of which is hereby incorporated by reference in their entirety.

GOVERNMENTAL RIGHTS

This invention was made with government support under AR052293 awarded by the National Institutes of Health. The government has certain rights in the invention.

FIELD OF THE INVENTION

The invention encompasses an amino acid composition for recovery of muscle strength and function during rehabilitation from a traumatic injury or major surgery, after physical exercise, or after extended bed rest.

BACKGROUND OF THE INVENTION

Incidences of major muscle tissue damage, such as traumas, reconstructive surgical procedures, and osteoporotic fractures or falls are associated with increased morbidity and mortality in older adults. Bone fractures are among the most common causes for acute admission to orthopedic wards with a 30% mortality rate 12-months post surgery. It was reported that such traumas produced a mean loss of 30% of retirement savings, and planned retirement age increased to 65 years from 64 years. Moreover, less than 50% of patients return to pre-trauma levels of mobility and independence, with older adults who survive a hip fracture being three times more likely to be functionally dependent, 50% requiring long-term assistance with routine functional activities and up to 25% requiring full-time residential care.

A contributing factor is the muscle atrophy associated with patients after extensive traumatic injury such as broken bones and surgical reconstructive procedures. Muscle atrophy is due to a metabolic response to stress that causes a preferential loss of muscle at a rate greater than would be expected from the lack of nutritional intake alone. Conventional nutritional management aimed at addressing muscle atrophy in trauma patients involves the provision of high energy, high protein diets. However the evidence for this approach is largely unconvincing. Hence, there is a need for a nutritional supplement to expedite the recovery of muscle strength and function in patients post-trauma or surgery.

DETAILED DESCRIPTION OF THE INVENTION

The present invention encompasses a composition comprising a specific amino acid formulation capable of improving the recovery of muscle strength and function, wherein recovery of muscle strength and function of the subject is improved relative to a subject that did not receive said amino acid composition. The composition may improve the recovery of muscle strength and function during rehabilitation from major muscle damage due to trauma, extended bed rest or from intense physical exercise. According to the invention, it was discovered that a formulation containing free essential amino acids (EAA) and arginine in specific amounts, is optimal for improvement in muscle recovery. In particular, it has been discovered that nutritional compositions comprising a mixture of essential amino acids and arginine, including substantial amounts of leucine, effectively stimulate recovery of muscle strength and function during rehabilitation from major surgery, traumatic injury or intense physical exercise. Advantageously, the formulation was found to be effective in older adults where recovery of muscle strength after muscle damage is problematic.

(a) Composition

The method of the invention comprises an amino acid composition. In some embodiments, the composition may comprise the essential amino acids histidine, isoleucine, leucine, lysine, methionine, phenylalanine, threonine, valine, and tryptophan. In preferred embodiments, the composition may comprise the amino acid arginine in addition to the essential amino acids histidine, isoleucine, leucine, lysine, methionine, phenylalanine, threonine, valine, and tryptophan.

In general, the amino acids may be L-amino acids, D-amino acids or mixtures thereof. In preferred embodiments, the amino acids are L-amino acids. Those of skill in the art will appreciate that the amino acids of the composition may be free amino acids or amino acids salts. The amino acid composition of the invention may also be in the form of intact protein or peptide, provided that the protein or peptide comprises the amino acids of the invention in the correct concentrations relative to each other. In preferred embodiments, the amino acids of the invention are free amino acids or amino acid salts.

The amino acids may be the canonical amino acids histidine, isoleucine, leucine, lysine, methionine, phenylalanine, threonine, valine, tryptophan, and arginine, or non-canonical amino acid derivatives. Non-limiting examples of non-canonical amino acids that may be used in the invention include L-lysine acetate, derivatives of L-tyrosine, ornithine, keto acid analogs, hydrochloride salt (L-cysteine HCL.H2O), and N-acetyl derivatives of the various amino acids. In preferred embodiments, the amino acids used in the compositions and solutions of the present invention may be in free form or salt form.

The composition may comprise about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, or about 2.5 w/w % of histidine, about 8.5, 8.6, 8.7, 8.8, 8.9, 9, 9.1, 9.2, 9.3, 9.4, 9.5, 9.6, 9.7, 9.8, 10, 10.1, 10.2, 10.3, 10.4, 10.5, 10.6, 10.7, 10.8, 10.9, or about 11 w/w % of isoleucine, about 34.5, 34.6, 34.7, 34.8, 34.9, 35, 35.1, 35.2, 35.3, 35.4, 35.5, 35.6, 35.7, 35.8, 35.9, 36, 36.1, 36.2, 36.3, 36.4, 36.5, 36.6, 36.7, 36.8, 36.9, 37, 37.1, 37.2, 37.3, 37.4, 37.5, 37.6, 37.7, 37.8, 37.9, or about 38 w/w % of leucine, about 14, 14.1, 14.2, 14.3, 14.4, 14.5, 14.6, 14.7, 14.8, 14.9, 15, 15.1, 15.2, 15.3, 15.4, 15.5, 15.6, 15.7, 15.8, 15.9, 16, 16.1, 16.2, 16.3, 16.4, 16.5, 16.6, 16.7, 16.8, 16.9, or about 17 w/w % of lysine, about 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, or about 4 w/w % of methionine, about 5, 5.1, 5.2, 5.3, 5.4, 5.5, 5.6, 5.7, 5.8, 5.9, 6, 6.1, 6.2, 6.7, 6.8, 6.9, or about 7 w/w % of phenylalanine, about 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, or about 9.5 w/w % of threonine, about 8.5, 8.6, 8.7, 8.8, 8.9, 9, 9.1, 9.2, 9.3, 9.4, 9.5, 9.6, 9.7, 9.8, 9.9, 10, 10.1, 10.2, 10.3, 10.4, 10.5, 10.6, 10.7, 10.8, 10.9, or about 11 w/w % of valine, about 0, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, or about 0.25 w/w % of tryptophan, and about 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 10, 10.1, 10.2, 10.3, 10.4, 10.5, 10.6, 10.7, 10.8, 10.9, or about 11 w/w % of arginine.

In some embodiments, the composition comprises about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, or about 2.5 w/w % of histidine. In other embodiments, the composition comprises about 0.5, 0.6, 0.7, 0.8, 0.9, or about 1 w/w % of histidine. In yet other embodiments, the composition comprises about 1, 1.1, 1.2, 1.3, 1.4, or about 1.5 w/w % of histidine. In other embodiments, the composition comprises about 1.5, 1.6, 1.7, 1.8, 1.9, or about 2 w/w % of histidine. In additional embodiments, the composition comprises about 2, 2.1, 2.2, 2.3, 2.4, or about 2.5 w/w % of histidine. In a preferred embodiment, the composition comprises about 1.4, 1.5, or about 1.6 w/w % of histidine.

In some embodiments, the composition comprises about 8.5, 8.6, 8.7, 8.8, 8.9, 9, 9.1, 9.2, 9.3, 9.4, 9.5, 9.6, 9.7, 9.8, 10, 10.1, 10.2, 10.3, 10.4, 10.5, 10.6, 10.7, 10.8, 10.9, or about 11 w/w % of isoleucine. In other embodiments, the composition comprises about 8.5, 8.6, 8.7, 8.8, 8.9, or about 9 w/w % of isoleucine. In yet other embodiments, the composition comprises about 9, 9.1, 9.2, 9.3, 9.4, or about 9.5 w/w % of isoleucine. In other embodiments, the composition comprises about 9.5, 9.6, 9.7, 9.8, or about 10 w/w % of isoleucine. In additional embodiments, the composition comprises about 10, 10.1, 10.2, 10.3, 10.4, or about 10.5 w/w % of isoleucine. In still other embodiments, the composition comprises about 10.5, 10.6, 10.7, 10.8, 10.9, or about 11 w/w % of isoleucine. In a preferred embodiment, the composition comprises about 9.6, 9.7, or about 9.8 w/w % of isoleucine.

In some embodiments, the composition may comprise about 34.5, 34.6, 34.7, 34.8, 34.9, 35, 35.1, 35.2, 35.3, 35.4, 35.5, 35.6, 35.7, 35.8, 35.9, 36, 36.1, 36.2, 36.3, 36.4, 36.5, 36.6, 36.7, 36.8, 36.9, 37, 37.1, 37.2, 37.3, 37.4, 37.5, 37.6, 37.7, 37.8, 37.9, or about 38 w/w % of leucine. In other embodiments, the composition may comprise about 34.5, 34.6, 34.7, 34.8, 34.9, 35, 35.1, 35.2, 35.3, 35.4, or about 35.5 w/w % of leucine. In yet other embodiments, the composition may comprise about 35.5, 35.6, 35.7, 35.8, 35.9, 36, 36.1, 36.2, 36.3, 36.4, or about 36.5 w/w % of leucine. In additional embodiments, the composition may comprise about 36.5, 36.6, 36.7, 36.8, 36.9, 37, 37.1, 37.2, 37.3, 37.4, or about 37.5 w/w % of leucine. In still other embodiments, the composition may comprise about 37.5, 37.6, 37.7, 37.8, 37.9, or about 38 w/w % of leucine. In a preferred embodiment, the composition comprises about 36.3, 36.4, or about 36.5 w/w % of leucine.

In some embodiments, the composition may comprise about 14, 14.1, 14.2, 14.3, 14.4, 14.5, 14.6, 14.7, 14.8, 14.9, 15, 15.1, 15.2, 15.3, 15.4, 15.5, 15.6, 15.7, 15.8, 15.9, 16, 16.1, 16.2, 16.3, 16.4, 16.5, 16.6, 16.7, 16.8, 16.9, or about 17 w/w % of lysine. In some embodiments, the composition may comprise about 14, 14.1, 14.2, 14.3, 14.4, 14.5, 14.6, 14.7, 14.8, 14.9, or about 15 w/w % of lysine. In some embodiments, the composition may comprise about 15, 15.1, 15.2, 15.3, 15.4, 15.5, 15.6, 15.7, 15.8, 15.9, or about 16 w/w % of lysine. In some embodiments, the composition may comprise about 16, 16.1, 16.2, 16.3, 16.4, 16.5, 16.6, 16.7, 16.8, 16.9, or about 17 w/w % of lysine. In a preferred embodiment, the composition may comprise about 15.1, 15.2, or about 15.3 w/w % of lysine.

In some embodiments, the composition may comprise about 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, or about 4 w/w % of methionine. In other embodiments, the composition may comprise about 2, 2.1, 2.2, 2.3, 2.4, or about 2.5 w/w % of methionine. In yet other embodiments, the composition may comprise about 2.5, 2.6, 2.7, 2.8, 2.9, or about 3 w/w % of methionine. In some embodiments, the composition may comprise about 3, 3.1, 3.2, 3.3, 3.4, or about 3.5 w/w % of methionine. In additional embodiments, the composition may comprise about 3.5, 3.6, 3.7, 3.8, 3.9, or about 4 w/w % of methionine. In a preferred embodiment, the composition may comprise about 2.9, 3, or about 3.1 w/w % of methionine.

In some embodiments, the composition may comprise about 5, 5.1, 5.2, 5.3, 5.4, 5.5, 5.6, 5.7, 5.8, 5.9, 6, 6.1, 6.2, 6.7, 6.8, 6.9, or about 7 w/w % of phenylalanine. In other embodiments, the composition may comprise about 5, 5.1, 5.2, 5.3, 5.4, or about 5.5 w/w % of phenylalanine. In yet other embodiments, the composition may comprise about 5.5, 5.6, 5.7, 5.8, 5.9, or about 6 w/w % of phenylalanine. In some embodiments, the composition may comprise about 6, 6.1, 6.2, 6.7, 6.8, 6.9, or about 7 w/w % of phenylalanine. In a preferred embodiment, the composition may comprise 6, 6.1, or about 6.2 w/w % of phenylalanine.

In some embodiments, the composition may comprise about 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, or about 9.5 w/w % of threonine. In other embodiments, the composition may comprise about 7.5, 7.6, 7.7, 7.8, 7.9, or about 8 w/w % of threonine. In additional embodiments, the composition may comprise about 8, 8.1, 8.2, 8.3, 8.4, or about 8.5 w/w % of threonine. In still other embodiments, the composition may comprise about 8.5, 8.6, 8.7, 8.8, 8.9, or about 9 w/w % of threonine. In some embodiments, the composition may comprise about 9, 9.1, 9.2, 9.3, 9.4, or about 9.5 w/w % of threonine. In a preferred embodiment, the composition may comprise about 8.4, 8.5, or about 8.6 w/w % of threonine.

In some embodiments, the composition may comprise about 8.5, 8.6, 8.7, 8.8, 8.9, 9, 9.1, 9.2, 9.3, 9.4, 9.5, 9.6, 9.7, 9.8, 10, 10.1, 10.2, 10.3, 10.4, 10.5, 10.6, 10.7, 10.8, 10.9, or about 11 w/w % of valine. In other embodiments, the composition may comprise about 8.5, 8.6, 8.7, 8.8, 8.9, or about 9 w/w % of valine. In yet other embodiments, the composition may comprise about 9, 9.1, 9.2, 9.3, 9.4, or about 9.5 w/w % of valine. In some embodiments, the composition may comprise about 9.5, 9.6, 9.7, 9.8, or about 10 w/w % of valine. In additional embodiments, the composition may comprise about 10, 10.1, 10.2, 10.3, 10.4, or about 10.5 w/w % of valine. In some embodiments, the composition may comprise about 10.5, 10.6, 10.7, 10.8, 10.9, or about 11 w/w % of valine. In a preferred embodiment, the composition may comprise about 9.9, 10, or about 10.1 w/w % of valine.

In some embodiments, the composition may comprise about 0, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, or about 0.25 w/w % of tryptophan. In other embodiments, the composition may comprise about 0, 0.01, 0.02, 0.03, 0.04, or about 0.05 w/w % of tryptophan. In yet other embodiments, the composition may comprise about 0.05, 0.06, 0.07, 0.08, 0.09, or about 0.1 w/w % of tryptophan. In some embodiments, the composition may comprise about 0.1, 0.11, 0.12, 0.13, 0.14, or about 0.15 w/w % of tryptophan. In other embodiments, the composition may comprise about 0.15, 0.16, 0.17, 0.18, 0.19, or about 0.2 w/w % of tryptophan. In additional embodiments, the composition may comprise about 0.2, 0.21, 0.22, 0.23, 0.24, or about 0.25 w/w % of tryptophan. In a preferred embodiment, the composition may comprise about 0.05, 0.06, or about 0.07 w/w % of tryptophan.

In some embodiments, the composition may comprise about 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 10, 10.1, 10.2, 10.3, 10.4, 10.5, 10.6, 10.7, 10.8, 10.9, or about 11 w/w % of arginine. In other embodiments, the composition may comprise about 7.5, 7.6, 7.7, 7.8, 7.9, 8, 8.1, 8.2, 8.3, 8.4, or about 8.5 w/w % of arginine. In yet other embodiments, the composition may comprise about 8.5, 8.6, 8.7, 8.8, 8.9, 9, 9.1, 9.2, 9.3, 9.4, or about 9.5 w/w % of arginine. In additional embodiments, the composition may comprise about 9.5, 9.6, 9.7, 9.8, 10, 10.1, 10.2, 10.3, 10.4, or about 10.5 w/w % of arginine. In some embodiments, the composition may comprise about 10.5, 10.6, 10.7, 10.8, 10.9, or about 11 w/w % of arginine. In a preferred embodiment, the composition may comprise about 8.9, 9, or about 9.1 w/w % of arginine.

In some embodiments, the composition may comprise the following concentrations of amino acids in terms of w/w %: about 1 to about 26 w/w % of histidine, about 9 to about 116 w/w % of isoleucine, about 35 to about 386 w/w % of leucine, about 14 to about 176 w/w % of lysine, about 2 to about 46 w/w % of methionine, about 5 to about 76 w/w % of phenylalanine, about 8 to about 96 w/w % of threonine, about 9 to about 116 w/w % of valine, about 0 to about 0.26 w/w % of tryptophan, and about 8 to about 116 w/w % of arginine. In exemplary embodiments, the composition may comprise about 1.4, 1.5, or about 1.6 w/w % of histidine, about 9.6, 9.7, or about 9.8 w/w % of isoleucine, about 36.3, 36.4, or about 36.5 w/w % of leucine, about 15.1, 15.2, or about 15.3 w/w % of lysine, about 2.9, 3, or about 3.1 w/w % of methionine, 6, 6.1, or about 6.2 w/w % of phenylalanine, 8.4, 8.5, or about 8.6 w/w % of threonine, 9.9, 10, or about 10.1 w/w % of valine, about 0.05, 0.06, or about 0.07 w/w % of tryptophan, and about 8.9, 9, or about 9.1 w/w % of arginine. In an especially exemplary embodiments, the composition may comprise about 1.5 w/w % of histidine, 9.7% of isoleucine, 36.4% of leucine, 15.2% of lysine, 3% of methionine, 6.1% of phenylalanine, 8.5% of threonine, 10% of valine, 0.06% of tryptophan, and 9% of arginine.

(b) Amino Acid Dose

As will be appreciated by one of skill in the art, the dose of the amino acid composition of the invention can and will vary depending on the body weight, sex, age and/or medical condition of the subject, the intensity of the physical exercise, the length of bed rest, the severity of the muscle damage or trauma suffered by the subject, the method of administration, and the duration of rehabilitation, as well as the species of the subject. Non-limiting examples of species may include a human, a companion animal, a lab animal, a zoo animal or an agricultural animal. Routine experimentation may readily establish the required dosage. Typical doses of the amino acid composition of the invention for oral administration may be about 15 g per dose. In some embodiments, a dose of about 5, 10, 15, 20, 25, 30, 35, 40, 45, 50, or 55 g of the amino acid composition may be administered. In other embodiments, a dose of about 5, 6, 7, 8, 9, 10, 11, 12, 13, 14, 15, 16, 17, 18, 19 or 20 g of the amino acid composition may be administered. In yet other embodiments, a dose of about 20, 21, 22, 23, 24, 25, 26, 27, 28, 29, 30, 31, 32, 33, 34, 35, 36, 37, 38, 39, or 40 g of the amino acid composition may be administered. In still other embodiments, a dose of about 30, 31, 32, 33, 34, 35, 36, 37, 38, 39, 40, 41, 42, 43, 44, 45, 46, 47, 48, 49, or 50 g of the amino acid composition may be administered. In an exemplary embodiment, the amino acid dose may be about 15 g per dose.

Administering multiple doses of the amino acid composition per day may also be used as needed to provide the desired level of recovery of muscle strength and function. For instance, one, two, three, four, or more doses of the amino acid composition may be administered per day. In a preferred embodiment, one dose of the amino acid composition may be administered per day. In another preferred embodiment, two doses of the amino acid composition may be administered per day. In yet another preferred embodiment, three doses of the amino acid composition may be administered per day.

The timing and duration of administration of the composition of the invention can and will vary. For instance, when the composition is administered to improve muscle strength and recovery from physical exercise, the composition may be administered before starting an exercise routine, during the exercise routine or after an exercise routine. Alternatively, when the composition is administered to improve muscle strength and recovery of a subject prone to muscle weakening such as an older human subject, the composition may be administered on a regular basis to maintain muscle strength and recovery. Or, when the composition is administered to improve muscle strength and recovery during rehabilitation from a post-traumatic injury, the composition may be administered throughout the post-traumatic rehabilitation period.

In some embodiments, when the composition is administered to improve muscle strength and recovery from physical exercise, the composition is administered before starting an exercise routine. In other embodiments, when the composition is administered to improve muscle strength and recovery from physical exercise, the composition is administered during the exercise routine. In yet other embodiments, when the composition is administered to improve muscle strength and recovery from physical exercise, the composition is administered after an exercise routine.

In some embodiments, when the composition is administered to improve muscle strength and recovery of a subject prone to muscle weakening such as an older human subject, the composition is administered on a regular basis to maintain muscle strength and recovery. In other embodiments, when the composition is administered to improve muscle strength and recovery during rehabilitation from a post-traumatic injury, the composition is administered throughout the post-traumatic rehabilitation period.

(c) Administration

The composition of the invention may be administered as intravenous, intramuscular, subcutaneous injection, intrapenal, intrarectal, vaginal administration, or parenteral routes. The amino acid composition of the invention may comprise a pharmaceutical carrier (or excipient). Such a carrier may be any solvent or solid material for encapsulation that is non-toxic. A carrier may give form or consistency, or act as a diluent. Suitable pharmaceutical carriers may include liquid carriers, such as normal saline and other non-toxic salts at or near physiological concentrations, and solid carriers not used for humans, such as talc or sucrose, or animal feed. Carriers may also include stabilizing agents, wetting and emulsifying agents, salts for varying osmolarity, encapsulating agents, buffers, and skin penetration enhancers. Carriers and excipients as well as formulations for parenteral and nonparenteral drug delivery are set forth in Remington's Pharmaceutical Sciences 19th Ed. Mack Publishing (1995).

In some embodiments, the composition may be formulated for parenteral administration (e.g., intraperitoneally, intravenously, subcutaneously, intramuscularly, etc.). Accordingly, these compositions are preferably combined with pharmaceutically acceptable vehicles such as saline, Ringer's solution, dextrose solution, and the like. For parenteral administration (including subcutaneous, intradermal, intravenous, intramuscular, and intraperitoneal), the composition may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil.

In a preferred embodiment, the amino acid composition of the invention may be administered orally. Non-limiting examples of oral formulations that may be used to administer the amino acid composition of the invention may be a nutritional formulation, a medical food, a medical beverage, a sports performance supplement, in the form of a complete meal, part of a meal, as a food additive as a powder for dissolution, in the form of a pharmaceutical formulation such as in the form of a tablet, pill, sachet or capsule or by tube feeding such as by means of nasogastric, nasoduodenal, esophagostomy, gastrostomy, or jejunostomy tubes, or peripheral or total parenteral nutrition. In an exemplary embodiment, the compositions of the invention may be administered orally as a dietary supplement.

Compositions for oral administration generally contain inert excipients in addition to the amino acid ingredients of the composition. Oral preparations may be enclosed in gelatin capsules or compressed into tablets. Common excipients used in such preparations include pharmaceutically compatible fillers/diluents such as microcrystalline cellulose, hydroxypropyl methylcellulose, starch, lactose, sucrose, glucose, mannitol, sorbitol, dibasic calcium phosphate, or calcium carbonate; binding agents such as alginic acid, carboxymethylcellulose, microcrystalline cellulose, gelatin, gum tragacanth, or polyvinylpyrrolidone; disintegrating agents such as alginic acid, cellulose, starch, or polyvinylpyrrolidone; lubricants such as calcium stearate, magnesium stearate, talc, silica, or sodium stearyl fumarate; glidants such as colloidal silicon dioxide; sweetening agents such as sucrose or saccharin; flavoring agents such as peppermint, methyl salicylate, or citrus flavoring; coloring agents; and preservatives such as antioxidants (e.g., vitamin A, vitamin C, vitamin E, or retinyl palmitate), citric acid, or sodium citrate. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof.

The compositions according to the invention may be nutritionally complete, i.e. may include vitamins, minerals, trace elements as well as nitrogen, carbohydrate and fat and/or fatty acid sources so that they may be used as the sole source of nutrition supplying essentially all the required daily amounts of vitamins, minerals, carbohydrates, fat and/or fatty acids, proteins and the like.

(d) Subject

The method of the invention comprises administering the amino acid composition to a subject. Suitable subjects include animals such as mammals and humans. Non-limiting examples of suitable animals include companion animals such as cats, dogs, rodents, and horses; research animal such as mice, rats and other rodents; agricultural animals such as cows, cattle, pigs, goats, sheep, horses, deer, chickens and other fowl; zoo animals; and primates such as chimpanzees, monkeys, and gorillas. In a preferred embodiment, the subject is a mammal. In another preferred embodiment, the subject is a human.

The human subject may be of any age. In some embodiments, the human subject may be about 40, 45, 50, 55, 60, 65, 70, 75, 80, 85, 90, 95 years of age or older. In some preferred embodiments, the human subject is 40 years of age or older. In other preferred embodiments, the human subject is 45 years of age or older. In yet other preferred embodiments, the human subject is 50 years of age or older. In still other preferred embodiments, the human subject is 55 years of age or older. In other preferred embodiments, the human subject is 60 years of age or older. In yet other preferred embodiments, the human subject is 65 years of age or older. In still other preferred embodiments, the human subject is 70 years of age or older. In other preferred embodiments, the human subject is 75 years of age or older. In still other preferred embodiments, the human subject is 80 years of age or older. In yet other preferred embodiments, the human subject is 85 years of age or older. In still other preferred embodiments, the human subject is 90 years of age or older.

In some embodiments, the subject may be undergoing rehabilitation from a trauma. As used herein, "trauma" is a body wound or shock produced by sudden physical injury as from violence or accident or a physical wound or injury, such as a fracture, blow, or surgical procedure, which results in major muscle tissue damage. In some alternatives of the embodiments, the rehabilitation may be from a post-surgical trauma. In an exemplary alternative of the embodiments, the rehabilitation may be from a hip surgery trauma. In another exemplary alternative of the embodiments, the rehabilitation may be from a knee surgery trauma.

Methods of rehabilitation from a trauma are known in the art and may include cardiovascular and pulmonary rehabilitation, clinical electrophysiology, geriatric, integumentary, orthopedic, pediatric, or sports rehabilitation. Geriatric rehabilitation therapy covers a wide area of issues concerning people as they go through normal adult aging but is usually focused on the older adult. Geriatric physical therapy is used to target conditions that affect many people as they grow older and include but are not limited to arthritis, osteoporosis, cancer, Alzheimer's disease, hip and joint replacement, balance disorders, incontinence, etc. Sports rehabilitation therapy treats athletic injury management, including acute care, treatment and rehabilitation, prevention, and education. Orthopedic rehabilitation therapy manages, and treats disorders and injuries of the musculoskeletal system including rehabilitation after orthopaedic surgery. Orthopedic therapists are trained in the treatment of post-operative orthopedic procedures, fractures, acute sports injuries, arthritis, sprains, strains, back and neck pain, spinal conditions and amputations. In general, rehabilitation from a trauma may be any method of rehabilitation that may be used to improve muscle strength and function of a subject after a traumatic injury.

In other embodiments, the subject may be recovering from a physical exercise. During high-intensity muscular physical exercises, the rate of muscular work being performed may exceed the ability of the blood supply to deliver oxygen, creating a condition which induces reductive stress in muscle cells and may lead to muscle damage, impaired performance, muscle soreness, predisposition to injury and a prolonged recovery period. Non-limiting examples of physical exercises that may lead to muscle damage, impaired performance, muscle soreness, predisposition to injury and a prolonged recovery period may include flexibility exercises such as stretching, aerobic exercises such as cycling, swimming, walking, skipping rope, rowing, running, hiking or playing tennis, anaerobic exercises, such as weight training, functional training, eccentric training or sprinting, strength training, agility training, or eccentric training.

In yet other embodiments, the subject may be recovering from extended bed rest. The extended bed rest may be due to a prescribed medical treatment as a treatment for an illness or medical condition. Extended bed rest has deleterious physiological effects, including muscle atrophy and other forms of deconditioning such as arterial constriction.

(e) Improvement in Muscle Strength

The method of the invention improves recovery of muscle strength and function in a subject receiving the amino acid composition relative to recovery of muscle strength and function in a subject that did not receive said amino acid composition. Stated another way, the method of the invention improves recovery of muscle strength and function in a subject receiving the amino acid composition relative to recovery of muscle strength and function in a subject receiving usual care for muscle damage. As used herein, the term "usual care" may refer to care normally received by a subject to increase muscle strength after muscle damage. Usual care can and will vary depending on the nature of muscle damage, and may be as described in Section I(d) above.

Methods of measuring muscle strength and function and recovery of muscle strength and function are known in the art. In general, methods of measuring muscle strength and function vary depending on the muscle groups to be measured. For instance, abdominal muscle strength may be measured using a sit-up test. The chair stand may be used to measure lower body muscle strength and function. Also, the arm curl test may be used to measure upper body muscle strength. And leg strength may be measured using the maximum voluntary contraction (MVC), which measures the peak force produced by a muscle as it contracts while pulling against an immovable object. In some embodiments, muscle strength and function may be measured using the chair stand method. In other embodiments, muscle strength and function may be measured using the maximum voluntary contraction method.

In some embodiments, muscle strength and function may improve about 1, 2, 3, 4, 5, 6, 7, 8, 9, 10, 15, 20%/day or more over pre-trauma levels when measured using the chair stand functional measure at 2 weeks post surgery. In an exemplary alternative of the embodiments, muscle strength and function may improve about 5%/day over pre-trauma levels when measured using the chair stand functional measure at 2 weeks post surgery.

In other embodiments, muscle strength and function may improve about 5, 6, 7, 8, 9, 10, 11, 12, 13, 14, 15, 20, 25%/day or more over pre-trauma levels when measured using the chair stand functional measure at 8 weeks post surgery. In an exemplary alternative of the embodiments, muscle strength and function may improve about 7%/day over pre-trauma levels when measured using the chair stand functional measure at 8 weeks post surgery.

In yet other embodiments, muscle strength and function may improve about 1, 2, 3, 4, 5, 6, 7, 8, 9, 10, 15, 20%/day or more over pre-trauma levels when measured using maximal voluntary contraction at 8 weeks post surgery. In an exemplary alternative of the embodiments, muscle strength and function may improve about 4%/day over pre-trauma levels when measured using maximal voluntary contraction at 8 weeks post surgery.

Muscle strength and function may improve about 10, 50, 100, 150, 200, 300, 400, 500, 600, 700, 800, 900, 1000, 1100, 1200, 1300% or more over muscle strength levels two weeks post surgery when measured using maximal voluntary contraction at 8 weeks post surgery. In some embodiments, muscle strength and function may improve about 10, 50, 100, 150, or 200% over muscle strength levels two weeks post surgery when measured using maximal voluntary contraction at 8 weeks post surgery. In other embodiments, muscle strength and function may improve about 100, 150, 200, 250, or 300% over muscle strength levels two weeks post surgery when measured using maximal voluntary contraction at 8 weeks post surgery. In yet other embodiments, muscle strength and function may improve about 200, 250, 300, 350, or 400% over muscle strength levels two weeks post surgery when measured using maximal voluntary contraction at 8 weeks post surgery. In still other embodiments, muscle strength and function may improve about 300, 350, 400, 450, or 500% over muscle strength levels two weeks post surgery when measured using maximal voluntary contraction at 8 weeks post surgery. In other embodiments, muscle strength and function may improve about 400, 450, 500, 550, or 600% over muscle strength levels two weeks post surgery when measured using maximal voluntary contraction at 8 weeks post surgery. In additional embodiments, muscle strength and function may improve about 500, 550, 600, 650, or 700% over muscle strength levels two weeks post surgery when measured using maximal voluntary contraction at 8 weeks post surgery. In other embodiments, muscle strength and function may improve about 600, 650, 700, 750, or 800% over muscle strength levels two weeks post surgery when measured using maximal voluntary contraction at 8 weeks post surgery. In still other embodiments, muscle strength and function may improve about 800, 850, 900, 950, or 1000% over muscle strength levels two weeks post surgery when measured using maximal voluntary contraction at 8 weeks post surgery. In other embodiments, muscle strength and function may improve about 900, 950, 1000, 1050, or 1100% over muscle strength levels two weeks post surgery when measured using maximal voluntary contraction at 8 weeks post surgery. In preferred embodiments, muscle strength and function may improve about 700, 750, 800, 850, or 900% over muscle strength levels two weeks post surgery when measured using maximal voluntary contraction at 8 weeks post surgery.

EXAMPLES

The following examples illustrate various iterations of the invention.

Example 1

Essential Amino Acid Supplementation to Enhance Recovery of Muscle Strength and Function The effect of supplementation of EAA+arginine in subjects undergoing rehabilitation after hip or knee replacement surgery was investigated.

Subjects.

24 human subjects who have recently undergone hip or knee surgery were recruited and completed the study (Tables 1 and 2). 9 of the subjects were given the usual post-surgical care. The rest of the subjects were given a composition comprising EAA+arginine. 15 g of the EAA+arginine composition was delivered. The placebo group did not receive amino acids. The EAA group was given pre-configured doses containing 15 g of EAA capsules immediately following surgery and throughout 8 weeks of rehabilitation. Subjects were instructed to take 3 doses per day between meals. Subjects returned for routine clinical follow-up at 2 and 8 weeks post-surgery. Strength and functional measures were performed pre-surgery, and at the 2 and 8 week follow-up visits. The composition of the EAA drink is outlined in Table 3.

TABLE 1

Subject demographics in the usual care group

| Surgical ID | Age | Surgical Procedure | Gender |
|---|---|---|---|
| HC-1 | 59 | Hip resurfacing | M |
| HC-5 | 56 | Hip total | M |
| HC-9 | 45 | Hip total | M |
| HC-10 | 57 | Hip total | F |
| HC-14 | 62 | Hip resurfacing | F |
| HC-16 | 65 | Hip resurfacing | F |
| HAA-23 | 50 | Hip total | M |
| HC-27 | 47 | Hip total | M |
| HC-20 | 78 | Knee revision | M |

TABLE 2

Subject demographics in the amino acid group

| Surgical ID | Age | Surgical Procedure | Gender |
|---|---|---|---|
| HAA-3 | 52 | Hip total | M |
| HAA-4 | 52 | Hip total | M |
| HAA-6 | 51 | Hip total | F |
| HAA-7 | 45 | Hip total | M |
| HAA-11 | 53 | Hip total | M |
| HAA-17 | 52 | Hip resurfacing | M |
| HAA-18 | 68 | Hip revision | F |
| HAA-22 | 64 | Hip total | F |
| HAA-19 | 62 | Knee total | F |
| HAA-21 | 66 | Knee total | F |
| HAA-24 | 60 | Knee revision | F |
| HAA-25 | 63 | Knee total | F |
| HAA-26 | 71 | Knee revision | M |
| HAA-42 | 59 | Knee total | M |
| HAA-43 | 45 | Knee total | M |

TABLE 3

Amino acid composition

| Amino acid | Amount (g) | Proportion of total by wt. (%) |
|---|---|---|
| Histidine | 0.225 | 1.5 |
| Isoleucine | 1.455 | 9.7 |
| Leucine | 5.46 | 36.4 |
| Lysine | 2.28 | 15.2 |
| Methionine | 0.45 | 3 |
| Phenylalanine | 0.915 | 6.1 |
| Threonine | 1.275 | 8.5 |
| Valine | 1.5 | 10 |
| Tryptophan | 0.009 | 0.06 |
| Arginine | 1.35 | 9 |
| Total | 15 | 100 |

Figure 1:
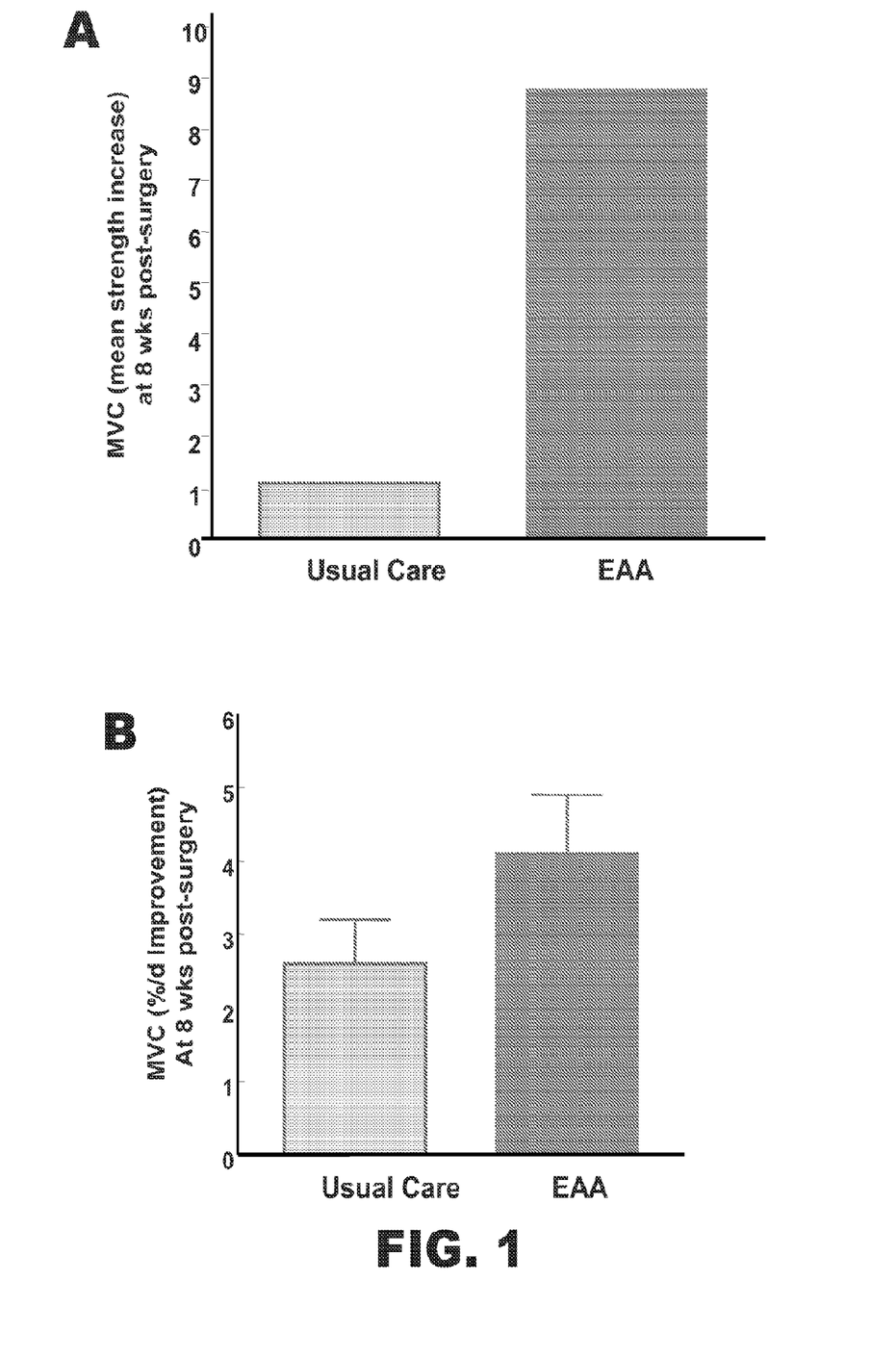
FIG. 1 depicts two graphs showing improvement in maximal voluntary contraction. (A) Mean strength improvement in maximal voluntary contraction from 2 to 8 weeks post joint replacement surgery in the affected/surgical side. (B) Improvement in maximal voluntary contraction over pre-surgical values at 8 weeks post joint replacement surgery in the affected/surgical side with data represented as mean±SEM and normalized by expressing as %/d improvement. Improvement from 2-8 weeks was significantly greater with EAA ($p<0.05$).
Figure 2:
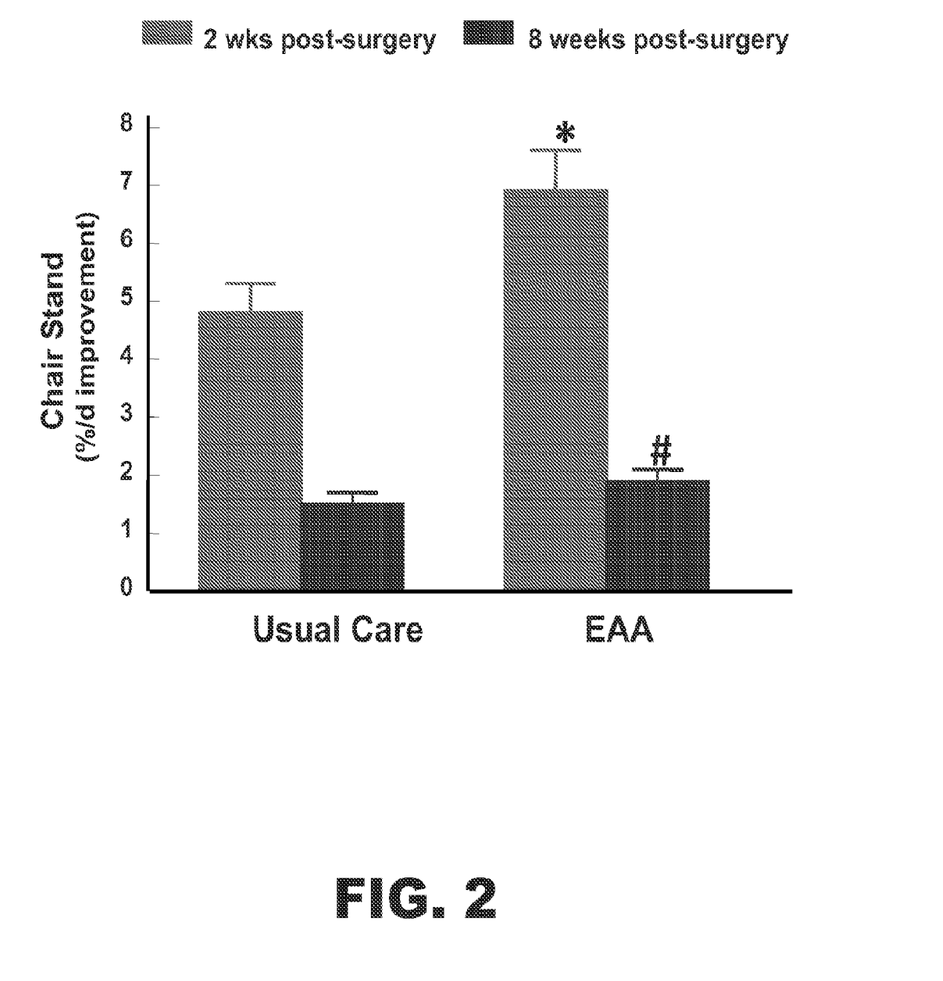
FIG. 2 depicts a graph showing improvement in the chair stand functional measure over pre-surgical values at 2 and 8 weeks post joint replacement surgery (surgical side). Data are mean±SEM and are normalized by expressing as %/d improvement. *; $P<0.04$, #; $p=0.08$.

Subjects performed the normal post-surgery rehabilitation, and muscle strength for both sets of subjects was measured using the maximal voluntary contraction measure and muscle function was assessed by the chair stand functional measure. Muscle strength measurements using maximal voluntary contraction showed a significantly better rate of improvement from 2 to 8 weeks in the patients receiving the EAA+arginine composition compared to the patients receiving the usual care 8 weeks after surgery (FIG. 1). Similarly, muscle function measurements using chair stand showed significantly better improvement in the patients receiving the EAA+arginine composition compared to the patients receiving the usual care 2 weeks and 8 weeks after surgery (FIG. 2).

Example 2

Amino Acid Supplementation for Improved Muscle Strength and Recovery after Physical Exercise The effect of supplementation of EAA+arginine after physical exercise may be investigated.

Subjects.

Human or animal subjects who regularly physically exercise may be recruited. Half of the subjects may be given a composition comprising EAA+arginine before during or after their exercise routine, whereas the rest of the subjects may be not be given the EAA+arginine composition. Muscle strength measurements may be performed before administration of the composition comprising EAA+arginine, and at regular intervals after administration of the composition. The composition of the EAA drink is outlined in Table 3.

Muscle strength measurements may show a significantly better rate of improvement from in subjects receiving the EAA+arginine composition compared to the patients not receiving the composition.

Example 3

Amino Acid Supplementation for Improved Muscle Strength and Recovery after Extended Bed Rest The effect of supplementation of EAA+arginine after extended bed rest may be investigated.

Subjects.

Human or animal subjects who are undergoing extended bed rest may be recruited. Half of the subjects may be given a composition comprising EAA+arginine before during or after the extended bed rest, whereas the rest of the subjects may be not be given the EAA+arginine composition. Muscle strength measurements may be performed before administration of the composition comprising EAA+arginine, and at regular intervals after administration of the composition. The composition of the EAA drink is outlined in Table 3.

Muscle strength measurements may show a significantly better rate of improvement from in subjects receiving the EAA+arginine composition compared to the patients not receiving the composition.

What is claimed is:

1. A method for improving recovery of muscle strength, the method comprising administering to a subject a composition comprising the following concentrations of amino acids in terms of w/w %: about 1 to 2% of histidine, about 9 to 11% of isoleucine, about 35 to 38% of leucine, about 14 to 17% of lysine, about 2 to 4% of methionine, about 5 to 7% of phenylalanine, about 8 to 9% of threonine, about 9 to 11% of valine, about 0.01 to 0.2% of tryptophan, and about 8 to 11% of arginine, wherein recovery of muscle strength of the subject is improved relative to recovery of muscle strength in a subject not administered said amino acid composition.

2. The method of claim 1, wherein muscle strength recovery is improved during rehabilitation from a post-surgical trauma.

3. The method of claim 2, wherein the subject is a human 40 years of age or older.

4. The method of claim 2, wherein the post-surgical trauma is selected from the group consisting of hip surgery trauma and knee surgery trauma.

5. The method of claim 1, wherein muscle strength and recovery is improved after physical exercise.

6. The method of claim 5, wherein a 15 g dose of the composition is administered to a human subject one, two, or three times a day.

7. The method of claim 1, wherein muscle strength improves about 4%/day over pre-trauma levels when measured using maximal voluntary contraction at 8 weeks post surgery.

8. The method of claim 1, wherein the composition comprises the following concentrations of amino acids in terms of w/w %: 1.5% of histidine, 9.7% of isoleucine, 36.4% of leucine, 15.2% of lysine, 3% of methionine, 6.1% of phenylalanine, 8.5% of threonine, 10% of valine, 0.06% of tryptophan, and 9% of arginine.

9. A method for improving muscle strength, the method comprising administering to a subject a composition comprising the following concentrations of amino acids in terms of w/w %: about 1 to 2% of histidine, about 9 to 11% of isoleucine, about 35 to 38% of leucine, about 14 to 17% of lysine, about 2 to 4% of methionine, about 5 to 7% of phenylalanine, about 8 to 9% of threonine, about 9 to 11% of valine, about 0.01 to 0.2% of tryptophan, and about 8 to 11% of arginine, wherein muscle strength of the subject is improved relative to muscle strength in a subject not administered said amino acid composition.

10. The method of claim 9, wherein muscle strength is improved during rehabilitation from a post-surgical trauma.

11. The method of claim 9, wherein muscle strength is improved after physical exercise.

12. The method of claim 11, wherein a 15 g dose of the composition is administered to a human subject one, two, or three times a day.

13. The method of claim 9, wherein the composition comprises the following concentrations of amino acids in terms of w/w %: 1.5% of histidine, 9.7% of isoleucine, 36.4% of leucine, 15.2% of lysine, 3% of methionine, 6.1% of phenylalanine, 8.5% of threonine, 10% of valine, 0.06% of tryptophan, and 9% of arginine.

14. A method for maintaining muscle strength, the method comprising administering to a subject a composition comprising the following concentrations of amino acids in terms of w/w %: about 1 to 2% of histidine, about 9 to 11% of isoleucine, about 35 to 38% of leucine, about 14 to 17% of lysine, about 2 to 4% of methionine, about 5 to 7% of phenylalanine, about 8 to 9% of threonine, about 9 to 11% of valine, about 0.01 to 0.2% of tryptophan, and about 8 to 11% of arginine, wherein muscle strength of the subject is maintained relative to muscle strength in a subject not administered said amino acid composition.

15. The method of claim 14, wherein muscle strength is maintained during rehabilitation from a post-surgical trauma.

16. The method of claim 14, wherein muscle strength is maintained after physical exercise.

17. The method of claim 16, wherein a 15 g dose of the composition is administered to a human subject one, two, or three times a day.

18. The method of claim 14, wherein the composition comprises the following concentrations of amino acids in terms of w/w %: 1.5% of histidine, 9.7% of isoleucine, 36.4% of leucine, 15.2% of lysine, 3% of methionine, 6.1% of phenylalanine, 8.5% of threonine, 10% of valine, 0.06% of tryptophan, and 9% of arginine.

* * * * *